US012746134B2

(12) United States Patent
Clevenger et al.

(10) Patent No.: US 12,746,134 B2
(45) Date of Patent: Sep. 29, 2026

(54) ANTI-MIGRATION STENT

(71) Applicant: BOSTON SCIENTIFIC SCIMED, INC., Maple Grove, MN (US)

(72) Inventors: Jasmine Clevenger, Sherborn, MA (US); Molly Solomon, Groton, MA (US); Jonathan Root, Townsend, MA (US); Kevin Windheuser, Hopkinton, MA (US); Garrett Casserly, Galway (IE); Michael Walsh, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 736 days.

(21) Appl. No.: 18/128,927

(22) Filed: Mar. 30, 2023

(65) Prior Publication Data

US 2023/0346577 A1 Nov. 2, 2023

Related U.S. Application Data

(60) Provisional application No. 63/325,797, filed on Mar. 31, 2022.

(51) Int. Cl.
*A61F 2/848* (2013.01)

(52) U.S. Cl.
CPC ........ *A61F 2/848* (2013.01); *A61F 2240/001* (2013.01)

(58) Field of Classification Search
CPC ..... A61F 2/848; A61F 2230/0091; A61F 2/07
See application file for complete search history.

(56) References Cited

U.S. PATENT DOCUMENTS

| | | | |
|---|---|---|---|
| 3,479,670 | A | 11/1969 | Medell |
| 5,129,910 | A | 7/1992 | Phan et al. |
| 5,556,426 | A | 9/1996 | Popadiuk et al. |
| 5,993,483 | A | 11/1999 | Gianotti |
| 6,776,194 | B2 | 8/2004 | Houston et al. |
| 7,384,428 | B2 | 6/2008 | Richter |

(Continued)

FOREIGN PATENT DOCUMENTS

| | | | |
|---|---|---|---|
| JP | 2011509758 | A | 3/2011 |
| JP | 201359643 | A | 4/2013 |

(Continued)

OTHER PUBLICATIONS

International Search Report and Written Opinion dated Jun. 27, 2023 for International Application No. PCT/US2023/016969.

*Primary Examiner* — Rebecca S Preston
(74) *Attorney, Agent, or Firm* — Seager, Tufte & Wickhem, LLP

(57) ABSTRACT

An endoprosthesis for implantation within a vessel lumen may include a tubular scaffold formed of one or more interwoven filaments, wherein the tubular scaffold is configured to shift between a radially collapsed configuration and a radially expanded configuration, a polymeric covering secured to the tubular scaffold, and an anti-migration element extending radially outward from the tubular scaffold. The anti-migration element extends helically along at least a portion of the length of the tubular scaffold in a first helical direction. The anti-migration element may include a wire extending along an outer surface of the tubular scaffold. The anti-migration element may include a second polymeric covering disposed over the wire.

20 Claims, 18 Drawing Sheets

(56) References Cited

U.S. PATENT DOCUMENTS

| | | | |
|---|---|---|---|
| 7,803,180 B2 | 9/2010 | Burpee et al. | |
| 8,226,708 B1 | 7/2012 | Murch | |
| 8,435,283 B2 | 5/2013 | Jordan et al. | |
| 8,491,649 B2 | 7/2013 | Mach | |
| 9,415,196 B2 | 8/2016 | Jordan | |
| 9,439,790 B2 | 9/2016 | Clerc et al. | |
| 9,526,640 B2 | 12/2016 | Bertolino et al. | |
| 9,539,126 B2 | 1/2017 | Walsh et al. | |
| 9,839,508 B2 | 12/2017 | Walsh et al. | |
| 9,980,806 B2 | 5/2018 | Tan-Malecki et al. | |
| 10,117,760 B2 | 11/2018 | Mangiardi | |
| 10,201,440 B2 | 2/2019 | Mangiardi | |
| 10,245,165 B2 | 4/2019 | Mangiardi | |
| 10,426,641 B2 | 10/2019 | Clerc et al. | |
| 10,583,019 B2 | 3/2020 | Mangiardi | |
| 10,758,380 B2 | 9/2020 | Bluecher et al. | |
| 10,932,925 B2 | 3/2021 | Mangiardi | |
| 11,559,412 B2 | 1/2023 | Gilmartin et al. | |
| 2001/0023370 A1 | 9/2001 | Smith et al. | |
| 2009/0187240 A1* | 7/2009 | Clerc | A61F 2/848 623/1.22 |
| 2010/0100170 A1 | 4/2010 | Tan et al. | |
| 2013/0138219 A1 | 5/2013 | Toomey et al. | |
| 2014/0277395 A1 | 9/2014 | Firstenberg et al. | |
| 2015/0073529 A1* | 3/2015 | Fleury | A61F 2/848 623/1.13 |
| 2015/0342760 A1 | 12/2015 | Christakis et al. | |
| 2017/0014247 A1* | 1/2017 | Ryan | A61F 2/88 |
| 2020/0146803 A1 | 5/2020 | Bertolino et al. | |
| 2020/0197196 A1* | 6/2020 | Lydecker | A61F 2/848 |
| 2020/0214858 A1* | 7/2020 | Gilmartin | A61F 2/90 |
| 2020/0214958 A1 | 7/2020 | Goren et al. | |
| 2020/0222212 A1 | 7/2020 | Gilmartin et al. | |
| 2021/0121306 A1 | 4/2021 | Henchie et al. | |
| 2021/0186720 A1 | 6/2021 | Bluecher et al. | |
| 2021/0236259 A1 | 8/2021 | Mcnern et al. | |

FOREIGN PATENT DOCUMENTS

| | | |
|---|---|---|
| JP | 2015519969 A | 7/2015 |
| JP | 2022518155 A | 3/2022 |
| WO | 2019099080 A1 | 5/2019 |
| WO | 2021086936 A1 | 5/2021 |

* cited by examiner

ANTI-MIGRATION STENT

CROSS-REFERENCE TO RELATED APPLICATIONS

This application claims the benefit of U.S. Provisional Patent Application Ser. No. 63/325,797, filed Mar. 31, 2022, which is incorporated herein by reference.

TECHNICAL FIELD

The present disclosure pertains to medical devices, and methods for manufacturing and/or using medical devices. More particularly, the present disclosure pertains to an improved design for an endoprosthesis or stent.

BACKGROUND

Stents, grafts, stent-grafts, and similar implantable medical devices, collectively referred to hereinafter as stents, are radially expandable or self-expanding endoprostheses which are intravascular or endoscopic implants capable of being implanted transluminally either percutaneously or endoscopically. Stents may be implanted in a variety of body lumens or vessels such as within the vascular system, urinary tracts, bile ducts, gastro-intestinal tract, airways, etc. Stents may be used to open constricted body lumens. Stents may be used to reinforce body vessels and to prevent restenosis following angioplasty in the vascular system. They may be self-expanding, mechanically expandable, or hybrid expandable. In general, self-expanding stents are mounted on a delivery device consisting of two tubes. The stent is delivered by sliding the outer tube to uncover and release the stent.

Stents are typically tubular members that are radially expandable from a reduced diameter configuration for delivery through a patient's body lumen to an expanded configuration once deployed at the treatment site. The stent may be formed from a tubular member in which a pattern is subsequently formed by etching or cutting material from the tubular member, or it may be made from wires or filaments using techniques such as braiding, knitting, or weaving. Desirable stent properties include sufficient flexibility to be able to conform to the tortuous body lumen during delivery, yet sufficient rigidity to resist migration once deployed at the treatment site.

In some stents, the compressible and flexible properties that assist in stent delivery may also result in a stent that tends to migrate from its originally deployed position. Stent migration affects many endoscopic stents including esophageal, duodenal, colonic, pancreatic, biliary and airway stents. It is thus desirable to provide a stent configuration that resists migration following deployment.

Some techniques that have been developed to prevent stent migration including adding barbs and flares to the stent itself or using clips or sutures to attach the stent to the vessel wall. However, there remains a need for an improved stent that is resistant to migration.

SUMMARY

In one example, an endoprosthesis for implantation within a vessel lumen may comprise a tubular scaffold having a length, the tubular scaffold formed of one or more interwoven filaments defining interstices therebetween, wherein the tubular scaffold is configured to shift between a radially collapsed configuration and a radially expanded configuration, a polymeric covering secured to the tubular scaffold, and an anti-migration element extending radially outward from the tubular scaffold. The anti-migration element may extend helically along at least a portion of the length of the tubular scaffold in a first helical direction.

In addition or alternatively to any example disclosed herein, the anti-migration element has a cross-sectional shape having a first circumferential width at a base and a second circumferential width at a radially outer tip that is greater than the first width.

In addition or alternatively to any example disclosed herein, the cross-sectional shape has a radially outer surface at the radially outer tip that is flat.

In addition or alternatively to any example disclosed herein, the anti-migration element comprises a wire extending along an outer surface of the tubular scaffold.

In addition or alternatively to any example disclosed herein, the wire is secured to the tubular scaffold at a plurality of attachment points.

In addition or alternatively to any example disclosed herein, the endoprosthesis may further comprise a second polymeric covering disposed over the wire and the plurality of attachment points.

In addition or alternatively to any example disclosed herein, the anti-migration element extends continuously from a proximal end of the anti-migration element to a distal end of the anti-migration element.

In addition or alternatively to any example disclosed herein, the anti-migration element extends discontinuously from a proximal end of the anti-migration element to a distal end of the anti-migration element such that a plurality of individual segments of the anti-migration element are spaced apart from one another.

In addition or alternatively to any example disclosed herein, each individual segment of the plurality of individual segments extends circumferentially less than one full revolution around the tubular scaffold.

In addition or alternatively to any example disclosed herein, the endoprosthesis may further comprise a second anti-migration element extending radially outward from the tubular scaffold. The second anti-migration element may extend helically along at least a portion of the length of the tubular scaffold in a second helical direction opposite the first helical direction such that the anti-migration element intersects with the second anti-migration element at a plurality of intersection points.

In addition or alternatively to any example disclosed herein, the anti-migration element and the second anti-migration element may each extend a first radial distance outward from the tubular scaffold between intersection points. The plurality of intersection points may extend the first radial distance outward from the tubular scaffold.

In addition or alternatively to any example disclosed herein, the anti-migration element and the second anti-migration element may each extend a first radial distance outward from the tubular scaffold between intersection points. The plurality of intersection points may extend a second radial distance outward from the tubular scaffold greater than the first radial distance.

In addition or alternatively to any example disclosed herein, a pitch between adjacent windings of the anti-migration element varies along the length of the tubular scaffold.

In addition or alternatively to any example disclosed herein, the pitch between adjacent windings of the anti-migration element is wider along a medial region of the tubular scaffold than the pitch between adjacent windings of the anti-migration element along a proximal end region of the tubular scaffold and/or a distal end region of the tubular scaffold.

In addition or alternatively to any example disclosed herein, the anti-migration element includes a first anti-migration element including a first plurality of helical windings disposed along a proximal end region of the tubular scaffold and a second anti-migration element including a second plurality of helical windings disposed along a distal end region of the tubular scaffold, the second anti-migration element being longitudinally spaced apart from the first anti-migration element by a medial region of the tubular scaffold.

In addition or alternatively to any example disclosed herein, a method of manufacturing an endoprosthesis for implantation within a vessel lumen may comprise forming a tubular scaffold from one or more interwoven filaments defining interstices therebetween, the tubular scaffold having a length; applying a polymeric covering to at least a portion of the tubular scaffold; positioning the tubular scaffold under a nozzle configured to apply a polymeric bead of material onto the polymeric covering; and applying the polymeric bead of material onto the polymeric covering previously applied to the tubular scaffold using the nozzle such that the polymeric bead of material forms an anti-migration element extending radially outward from the polymeric covering, wherein the anti-migration element extends helically along at least a portion of the length of the tubular scaffold.

In addition or alternatively to any example disclosed herein, the method may further comprise rotating and moving the tubular scaffold longitudinally relative to the nozzle to vary a pitch between adjacent windings of the anti-migration element.

In addition or alternatively to any example disclosed herein, a method of manufacturing an endoprosthesis for implantation within a vessel lumen may comprise forming a tubular scaffold from one or more interwoven filaments defining interstices therebetween, the tubular scaffold having a length; applying a polymeric covering to at least a medial region of the tubular scaffold; wrapping a wire helically around the tubular scaffold over the polymeric covering; securing the wire to uncovered portions of the tubular scaffold; and thereafter, applying a second polymeric covering over the wire and the uncovered portions of the tubular scaffold.

In addition or alternatively to any example disclosed herein, the uncovered portions of the tubular scaffold include a proximal end region disposed proximal of the medial region and a distal end region disposed distal of the medial region.

In addition or alternatively to any example disclosed herein, the uncovered portions of the tubular scaffold include a plurality of attachment points of the tubular scaffold defined by removing some of the polymeric covering from the tubular scaffold. Securing the wire to uncovered portions of the tubular scaffold may include securing the wire to the tubular scaffold at the plurality of attachment points.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
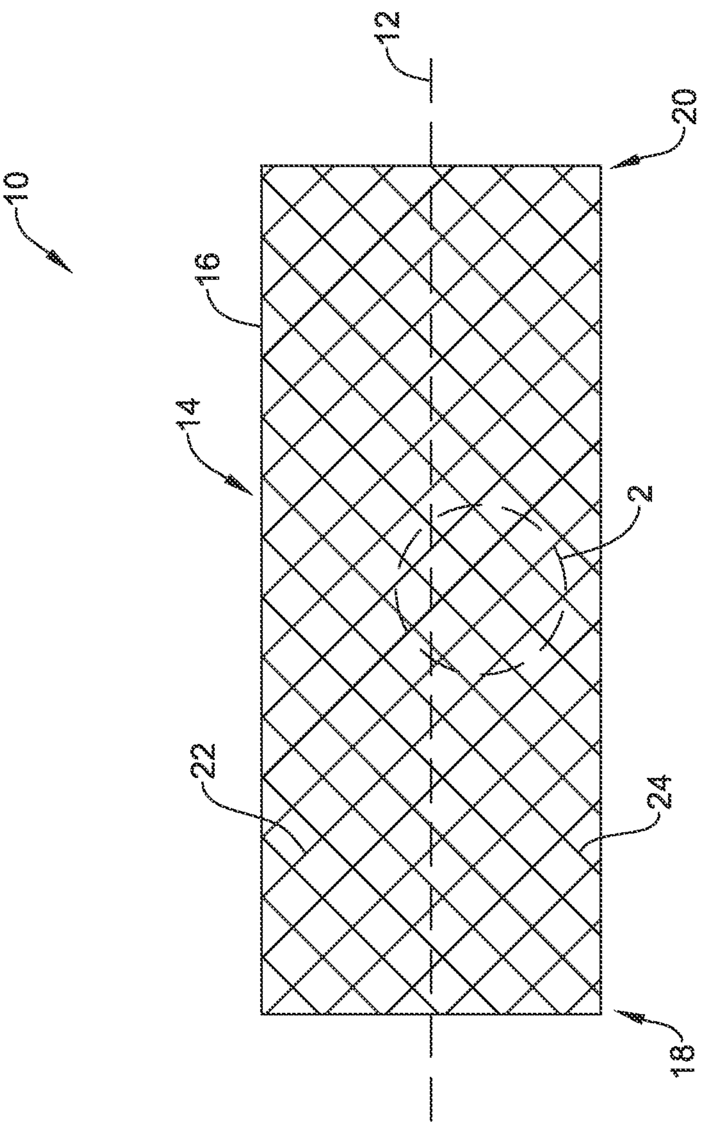
FIG. 1 is a schematic illustration of selected aspects of an endoprosthesis.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate exemplary aspects of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, all elements of the disclosure are not necessarily shown in each figure or discussed in detail below. However, it will be understood that the following discussion may apply equally to any and/or all of the components for which there are more than one, unless explicitly stated to the contrary.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered the greatest possible dimension measured according to the intended usage, while a "minimum extent" may be considered the smallest possible dimension measured according to the intended usage. In some instances, an "extent" may generally be measured orthogonally within a plane and/or cross-section, but may be, as will be apparent from the particular context, measured differently-such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The figures illustrate selected components and/or arrangements of an endoprosthesis or stent. It should be noted that in any given figure, some features of the endoprosthesis or stent may not be shown, or may be shown schematically, for simplicity. Additional details regarding some of the components of the endoprosthesis or stent may be illustrated in other figures in greater detail. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the filament", "the cell", "the strut", or other features may be equally referred to all instances and quantities beyond one of said feature. As such, it will be understood that the following discussion may apply equally to any and/or all of the components for which there are more than one within the endoprosthesis or stent, unless explicitly stated to the contrary. Additionally, not all instances of some elements or features may be shown in each figure for clarity.

FIG. 1 is a schematic illustration of an endoprosthesis 10. The term "stent" may be used interchangeably with the term "endoprosthesis" herein. The endoprosthesis 10 may be defined by and/or may have a central longitudinal axis 12 extending between a first end 18 and a second end 20. The endoprosthesis 10 may include a tubular scaffold 16 defining an outer surface 14 that is generally cylindrical. The tubular scaffold 16 may extend from the first end 18 to the second end 20. The tubular scaffold 16 may include a lumen extending longitudinally therethrough from the first end 18 to the second end 20. In some embodiments, the first end 18 may be a proximal end and the second end 20 may be a distal end. In some embodiments, the endoprosthesis 10 and/or the tubular scaffold 16 may include a proximal end region, a distal end region, and a medial region extending between the proximal end region and the distal end region. In some embodiments, the proximal end region may include a flared first end portion (not shown). In some embodiments, the distal end region may include a flared second end portion (not shown). In some embodiments, the tubular scaffold 16 may include a body portion extending along the medial region and/or between the flared first end portion and the flared second end portion of the endoprosthesis 10. Other configurations are also contemplated. The endoprosthesis 10 and/or the tubular scaffold 16 may be configured to shift between a radially collapsed configuration and a radially expanded configuration. Thus, the endoprosthesis 10 and/or the tubular scaffold 16 may be radially expandable from a radially constrained delivery configuration to a radially expanded deployed configuration. In some embodiments, the endoprosthesis 10 and/or the tubular scaffold 16 may be self-expandable, mechanically expandable, or balloon expandable. Other configurations are also contemplated.

Figure 2:
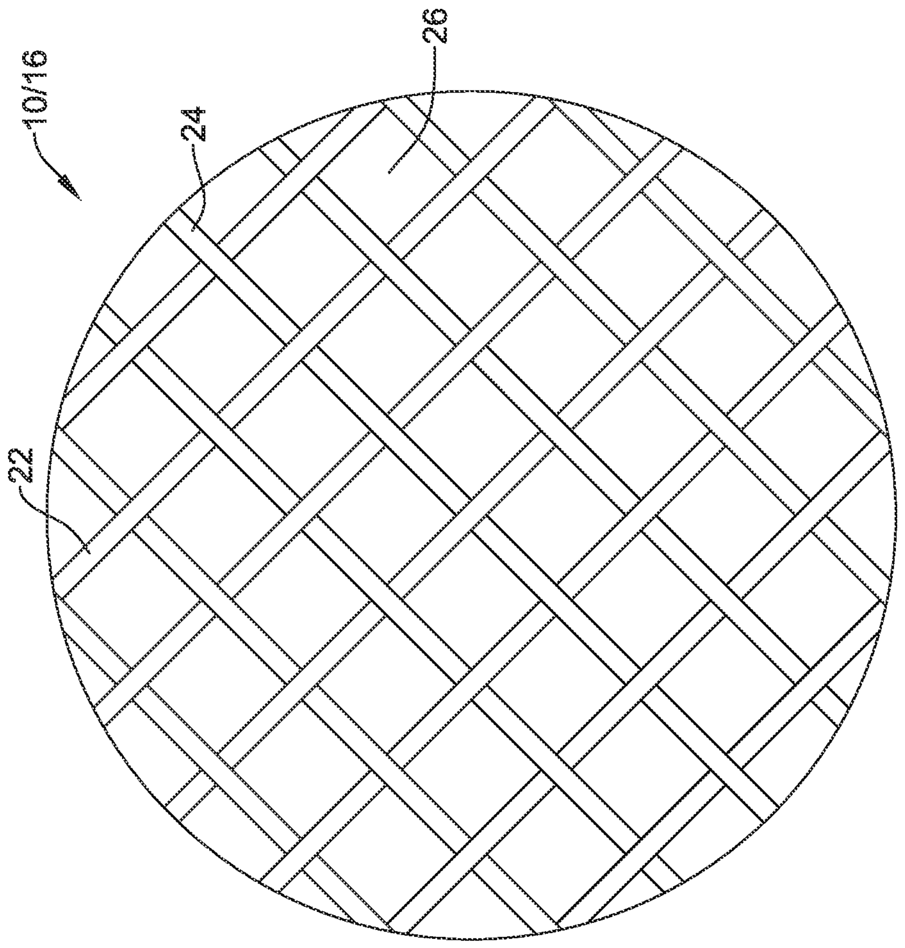
FIG. 2 is a detailed view illustrating selected aspects of the endoprosthesis of FIG. 1.

FIG. 2 is a detailed view illustrating a portion of the endoprosthesis 10. In some embodiments, the endoprosthesis 10 and/or the tubular scaffold 16 may be formed of one or more interwoven filaments defining interstices 26 (e.g., openings) therebetween. In some embodiments, the one or more interwoven filaments may include a first filament 22 extending around the central longitudinal axis 12 in a first helical direction and a second filament 24 extending around the central longitudinal axis 12 in a second helical direction. In some embodiments, the one or more interwoven filaments may include a plurality of first filaments extending around the central longitudinal axis 12 in a first helical direction and a plurality of second filaments extending around the central longitudinal axis 12 in a second helical direction. In some embodiments, the one or more interwoven filaments may form a braided tubular scaffold in which the first filaments intersect the second filaments and cross over and/or cross under the second filaments at a plurality of cross-over locations. The one or more interwoven filaments may define the outer surface 14 (e.g., FIG. 1) of the endoprosthesis 10. In some embodiments, the one or more interwoven filaments may include wire(s), thread(s), strand(s), etc.

In some embodiments, the one or more interwoven filaments may extend in helical directions while crossing over and under one another along the length of the tubular scaffold 16. In some embodiments, the first filament 22 and/or the plurality of first filaments may extend in a first helical path around the central longitudinal axis 12 in a first direction (e.g., a first helical direction) from the first end 18 toward and/or to the second end 20. In some embodiments, the first direction may be clockwise. In some embodiments, the second filament 24 and/or the plurality of second filaments may extend in a second helical path around the central longitudinal axis 12 in a second direction (e.g., a second helical direction) from the first end 18 toward and/or to the second end 20. In some embodiments, the second direction may be opposite the first direction. In some embodiments, the second direction may be counterclockwise. Other configurations are also contemplated.

In some alternative configurations, the endoprosthesis 10 and/or the tubular scaffold 16 may be cut from a tube as a monolithic structure. In some alternative configurations, the endoprosthesis and/or the tubular scaffold 16 may be cut from a flat sheet, rolled to form a tubular structure and/or shape, and then welded together to form the tubular scaffold 16. In some alternative configurations, the endoprosthesis 10 and/or the tubular scaffold 16 may be knitted, woven, or otherwise assembled. Other configurations are also contemplated. Some suitable but non-limiting materials for the endoprosthesis 10, the tubular scaffold 16, the first filament 22, the second filament 24, and/or components or elements thereof, for example metallic materials and/or polymeric materials, are described below.

The endoprosthesis 10 and/or the tubular scaffold 16 may be substantially tubular and/or may include a lumen extending axially therethrough along the central longitudinal axis 12 of the endoprosthesis 10 and/or the tubular scaffold 16 from the first end 18 to the second end 20. In some embodiments, the endoprosthesis 10 and/or the tubular scaffold 16 may have a length measured from the first end 18 to the second end 20 of about 20 millimeters to about 250 millimeters, about 40 millimeters to about 225 millimeters, about 60 millimeters to about 200 millimeters, about 80 millimeters to about 175 millimeters, about 100 millimeters to about 150 millimeters, or another suitable range. In some embodiments, the endoprosthesis 10 and/or the tubular scaffold 16 may have a radial outer dimension or radial extent of about 2 millimeters to about 30 millimeters, about 5 millimeters to about 25 millimeters, about 8 millimeters to about 20 millimeters, about 10 millimeters to about 15 millimeters, or another suitable range. Other configurations are also contemplated.

In some embodiments, the endoprosthesis 10 may be used in conjunction with a stent delivery system (not shown) for delivery and/or implantation of the endoprosthesis 10 in a body lumen. The system may include an elongate tubular member (e.g., an outer tubular member) having a lumen extending therein and/or therethrough. In some alternative embodiments, the elongate tubular member may include a plurality of lumens extending therein and/or therethrough. In at least some embodiments, the system may include an elongate inner member disposed within the lumen of the elongate tubular member. In some embodiments, the elongate inner member may be a tubular member having a lumen extending therein and/or therethrough. In some embodiments, the lumen of the elongate inner member may be a guidewire lumen. In some embodiments, the lumen of the elongate inner member may be used for irrigation and/or aspiration. Other configurations are also contemplated. In some alternative embodiments, the elongate inner member may be a solid shaft.

In some embodiments, the elongate inner member may be axially translatable relative to the elongate tubular member. In some embodiments, the elongate tubular member may be translatable in a proximal direction relative to the elongate inner member. For example, the elongate inner member may be held in a fixed position while the elongate tubular member is withdrawn proximally. In some embodiments, the elongate tubular member and the elongate inner member may be configured to be advanced to a target site together and/or simultaneously. In at least some embodiments, during advancement to the target site, the elongate tubular member and the elongate inner member may be disposed and/or held in an axially fixed relationship relative to each other. Other configurations are also contemplated.

In some embodiments, the endoprosthesis 10 may be disposed within the lumen of the elongate tubular member in the radially collapsed configuration. In some embodiments, the elongate tubular member may constrain the endoprosthesis 10 in the radially collapsed configuration when the endoprosthesis 10 is disposed within the lumen of the elongate tubular member. In some embodiments, the endoprosthesis 10 may be disposed radially between the elongate tubular member and the elongate inner member. In some embodiments, the endoprosthesis 10 may be attached to, crimped onto, and/or otherwise retained by the elongate inner member. Other configurations are also contemplated.

During delivery to a treatment site, the endoprosthesis 10 and/or the tubular scaffold 16 may be disposed within the lumen of the elongate tubular member in the radially collapsed configuration. Upon removal and/or release from the lumen of the elongate tubular member, the endoprosthesis 10 and/or the tubular scaffold 16 may shift and/or may be shifted from the radially collapsed configuration to the radially expanded configuration.

Figure 3:
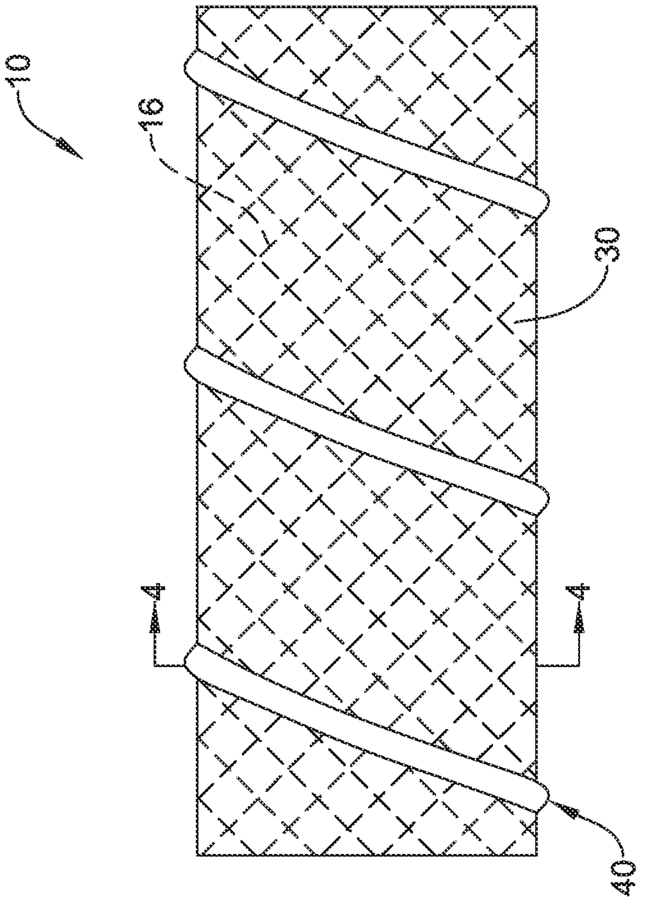
FIG. 3 illustrates selected aspects of the endoprosthesis of FIG. 1.

In some embodiments, the endoprosthesis 10 may include a polymeric covering 30 extending along and/or secured to the tubular scaffold 16, as seen in FIG. 3. In some embodiments, the tubular scaffold 16 may be completed covered with the polymeric covering 30. In some embodiments, the polymeric covering 30 may be coterminous with the tubular scaffold 16. In some embodiments, the polymeric covering 30 may be fixedly secured to, bonded to, or otherwise attached along and/or about the circumference of the tubular scaffold 16. In some embodiments, in at least some locations where the polymeric covering 30 touches the tubular scaffold 16, the polymeric covering 30 may be fixedly secured to, bonded to, or otherwise attached to the tubular scaffold 16. In some embodiments, the polymeric covering 30 may be fixedly secured to, bonded to, or otherwise attached to the tubular scaffold 16 at each and every location where the polymeric covering 30 touches the tubular scaffold 16. In some embodiments, the tubular scaffold 16, the one or more interwoven filaments, the first filament 22, the second filament 24, etc. and/or portions thereof, may be at least partially embedded within the polymeric covering 30. Other configurations are also contemplated.

In some embodiments, the polymeric covering 30 may extend along an entire length of the endoprosthesis 10 and/or the tubular scaffold 16. In some embodiments, the polymeric covering 30 may extend along a portion of the length of the endoprosthesis 10 and/or the tubular scaffold 16. In some embodiments, the polymeric covering 30 may extend continuously from the first end 18 of the endoprosthesis 10 and/or the tubular scaffold 16 to the second end 20 of the endoprosthesis 10 and/or the tubular scaffold 16. Other configurations are also contemplated. Some suitable but non-limiting materials for the polymeric covering 30, for example polymeric materials, are discussed below.

In some embodiments, the endoprosthesis 10 may include an anti-migration element 40 extending radially outward from the tubular scaffold 16. In some embodiments, the anti-migration element 40 may extend radially outward from the polymeric covering 30. In some embodiments, the anti-migration element 40 may be fixedly secured to, bonded to, or otherwise attached to the tubular scaffold 16 and/or the polymeric covering 30. In at least some embodiments, the anti-migration element 40 may extend helically along at least a portion of the length of the tubular scaffold 16 in a first helical direction (e.g., clockwise). In some embodiments, the tubular scaffold 16, or a portion thereof, may have maintain a constant outer diameter, with the anti-migration element 40 extending radially outward from the constant outer diameter of the tubular scaffold 16.

In some embodiments, the anti-migration element 40 may be formed from a polymeric material. In some embodiments, the anti-migration element 40 may be applied to and/or bonded to the outer surface of the polymeric covering 30 during a subsequent manufacturing step after the polymeric covering 30 has been applied to the tubular scaffold 16 and cured. In some embodiments, the anti-migration element 40 may be formed from a polymeric bead of material applied over the polymeric covering 30. Some suitable but non-limiting materials for the anti-migration element 40 and/or the polymeric bead of material, for example polymeric materials, are described below. In one non-limiting example, the anti-migration element 40 and/or the polymeric bead of material may be formed from silicone or polyamide. In some embodiments, the anti-migration element 40 and/or the polymeric bead of material may be formed from the same polymeric material as the polymeric covering 30 or a different polymeric material than the polymeric covering 30. Other configurations are also contemplated.

In some embodiments, the anti-migration element 40 may be bioabsorbable and/or may include a bioabsorbable material. In some embodiments, the anti-migration element 40 may include an adhesive material and/or a bioadhesive material. In some embodiments, the bioadhesive material may include natural polymeric materials, as well as synthetic materials, and synthetic materials formed from biological monomers such as sugars. In some embodiments, the bioadhesives are designed to adhere to biological tissue. For example, the anti-migration element 40 may be configured to adhere to tissue in situ. Some examples of bioadhesives may include, but are not limited to, mucoadhesives, amino adhesives, adhesive surface proteins, adhesively modified polymers, catechol moieties, polymer materials, polysaccharides, hydrogels, cross-linked or uncross-linked minigel particles, and so forth, as well as mixtures and/or combinations thereof.

In some embodiments, the endoprosthesis 10 may be delivered with the adhesive material and/or the bioadhesive material in a substantially inert state. In the substantially inert state, the adhesive material and/or the bioadhesive material may be non-reactive and/or may exhibit non-adhesive properties with respect to adjacent elements of the endoprosthesis 10, the stent delivery system, and/or a body lumen. For example, in the substantially inert state, the adhesive material and/or the bioadhesive material may not adhere to the endoprosthesis, the elongate inner member, and/or the elongate tubular member. Additionally, in the substantially inert state, the adhesive material and/or the bioadhesive material may not adhere to the body lumen. In some embodiments, in the substantially inert state, the adhesive material and/or the bioadhesive material may be substantially dry, dehydrated, or devoid of moisture. In some embodiments, adding or introducing fluid(s), moisture, and/or a selected type of fluid to the adhesive material and/or the bioadhesive material may activate the adhesive material and/or the bioadhesive material. In situations and/or configurations where the adhesive material and/or the bioadhesive material is "sticky", "tacky", etc. with respect to adjacent structures and/or elements, the adhesive material and/or the bioadhesive material may be assumed to no longer be in the substantially inert state.

In some embodiments, wetting the adhesive material and/or the bioadhesive material with a fluid may activate the adhesive material and/or the bioadhesive material. In other instances, the adhesive material and/or the bioadhesive material may be activated by another stimulus. In at least some embodiments, the adhesive material and/or the bioadhesive material may be pressure sensitive. In some embodiments, the adhesive material and/or the bioadhesive material may be disposed radially outward of the endoprosthesis 10, the tubular scaffold 16, and/or the polymeric covering 30. In some embodiments, after deployment of the endoprosthesis 10, the radially outward expanding force exerted on the adhesive material and/or the bioadhesive material by the endoprosthesis 10 and/or the tubular scaffold 16 may activate the pressure sensitive adhesive material and/or bioadhesive material. Other configurations are also contemplated.

Figure 4A:
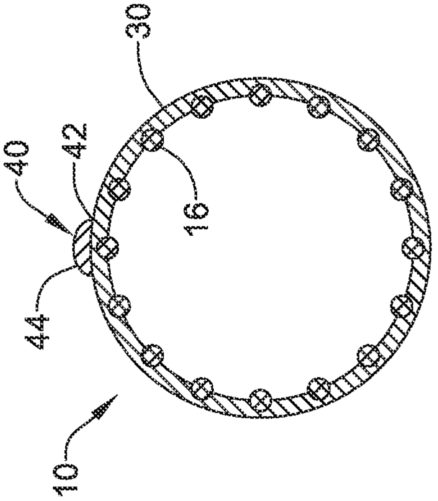
FIG. 4A is a partial cross-sectional view illustrating selected aspects of the endoprosthesis of FIG. 1.
Figure 4B:
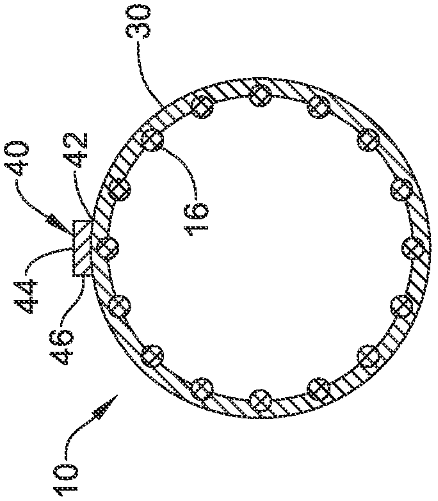
FIG. 4B is a partial cross-sectional view illustrating selected aspects of an alternative configuration of the endoprosthesis of FIG. 1.

FIGS. 4A-4D illustrate examples of a cross-sectional shape of the anti-migration element 40. The anti-migration element 40 may include a base 42 disposed immediately adjacent to the tubular scaffold 16 and/or the radially outward facing surface of the polymeric covering 30. In some embodiments, the anti-migration element 40 may have a cross-sectional shape having a radially outer surface (e.g., radially outward facing surface) 44 that is convexly curved, as seen in FIG. 4A. In some embodiments, the cross-sectional shape of the anti-migration element 40 may be domed, arched, and/or hemispherical. In some embodiments, the anti-migration element 40 may have a cross-sectional shape having a radially outer surface 44 that is flat or planar, as seen in FIG. 4B. In some embodiments, the cross-sectional shape of the anti-migration element 40 may be polygonal, square, rectangular, trapezoidal, etc. In some embodiments, the radially outer surface (e.g., radially outward facing surface) 44 may have no intersection point with and/or no direct contact with the tubular scaffold 16 and/or the polymeric covering 30. For example, in some embodiments, the radially outer surface 44 of the anti-migration element 40 may be radially spaced apart from the base 42 of the anti-migration element 40 by a side surface 46 of the anti-migration element 40. The side surface 46 may be distinct from and/or distinguishable from the radially outer surface 44. For example, the side surface 46 may intersect with the base 42 and/or the radially outer surface 44 at a non-zero angle, such as a perpendicular or oblique angle.

Figure 4C:
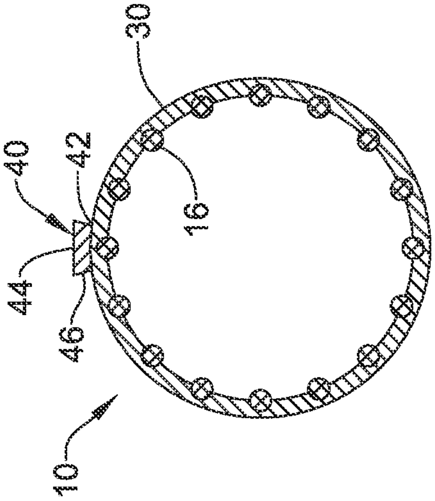
FIG. 4C is a partial cross-sectional view illustrating selected aspects of an alternative configuration of the endoprosthesis of FIG. 1.
Figure 4D:
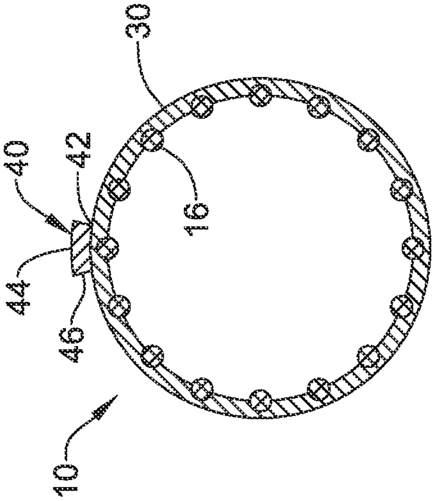
FIG. 4D is a partial cross-sectional view illustrating selected aspects of an alternative configuration of the endoprosthesis of FIG. 1.

In some embodiments, the anti-migration element 40 may have a cross-sectional shape having a first circumferential width at the base 42 and a second circumferential width at a radially outer tip that is greater than the first circumferential width at the base 42, as seen in FIGS. 4C and 4D. In some embodiments, the cross-sectional shape of the anti-migration element 40 has a radially outer surface 44 at the radially outer tip that is flat (e.g., FIG. 4C). In some embodiments, the cross-sectional shape of the anti-migration element 40 has a radially outer surface 44 at the radially outer tip that is curved (e.g., FIG. 4D), such as a convex curvature or a concave curvature. Other configurations are also contemplated.

Figure 5:
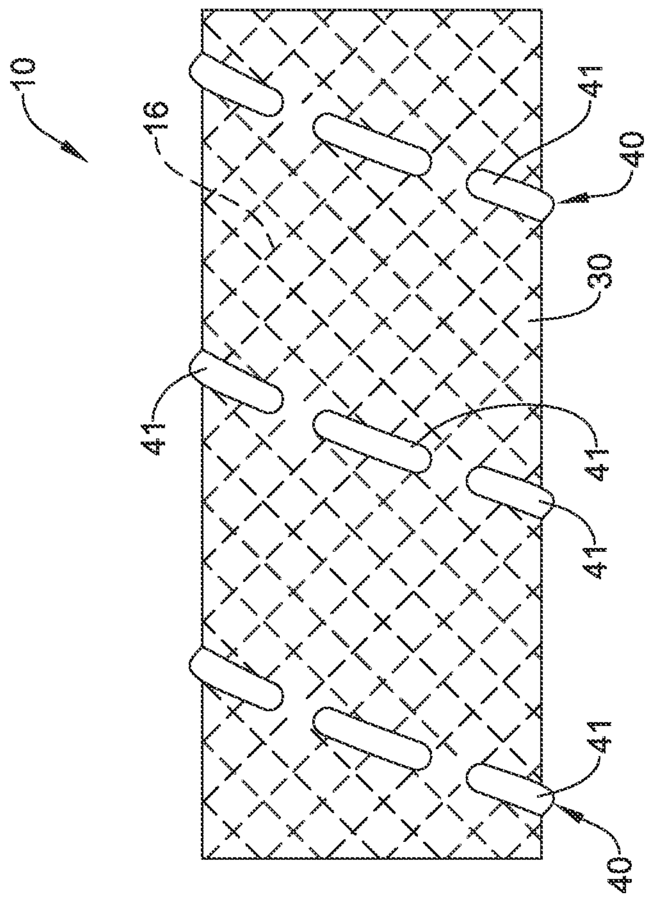
FIG. 5 illustrates selected aspects of an alternative configuration of the endoprosthesis of FIG. 1

In some embodiments, the anti-migration element 40 may extend continuously from a proximal end of the anti-migration element 40 to a distal end of the anti-migration element 40, as seen in FIG. 3 for example. In some instance the first end of the anti-migration element 40 may be located proximate the first end 18 of the endoprosthesis 10 or tubular scaffold 16 and/or the second end of the anti-migration element 40 may be located proximate the second end 20 of the endoprosthesis 10 and/or tubular scaffold 16. In some embodiments, the anti-migration element 40 may extend intermittently and/or discontinuously from a proximal end of the anti-migration element 40 to a distal end of the anti-migration element 40 such that a plurality of individual segments 41 of the anti-migration element 40 are spaced apart from one another, as seen in FIG. 5 for example. Thus, portions of the outer surface of the polymeric covering 30 may be visible helically between adjacent segments of the plurality of individual segments 41 of the anti-migration element 40. In at least some embodiments, the plurality of individual segments 41 of the anti-migration element 40 may be spaced apart circumferentially from one another.

In some embodiments, each individual segment of the plurality of individual segments 41 of the anti-migration element 40 may extend circumferentially more than one full revolution around a circumference of the tubular scaffold 16. In some embodiments, each individual segment of the plurality of individual segments 41 of the anti-migration element 40 may extend along an arc length of at least 360 degrees around the circumference of the tubular scaffold 16. In some embodiments, each individual segment of the plurality of individual segments 41 of the anti-migration element 40 may extend along an arc length of about 360 degrees around the circumference of the tubular scaffold 16.

In some embodiments, each individual segment of the plurality of individual segments 41 of the anti-migration element 40 may extend circumferentially less than one full revolution around the tubular scaffold 16. In some embodiments, each individual segment of the plurality of individual segments 41 of the anti-migration element 40 may extend along an arc length of less than 360 degrees around the circumference of the tubular scaffold 16. In some embodiments, each individual segment of the plurality of individual segments 41 of the anti-migration element 40 may extend along an arc length of 180 degrees or less, or less than 180 degrees around the circumference of the tubular scaffold 16. In some embodiments, each individual segment of the plurality of individual segments 41 of the anti-migration element 40 may extend along an arc length of 90 degrees or less, or less than 90 degrees around the circumference of the tubular scaffold 16. In some embodiments, each individual segment of the plurality of individual segments 41 of the anti-migration element 40 may extend along an arc length of 45 degrees or less, or less than 45 degrees around the circumference of the tubular scaffold 16. Other configurations are also contemplated.

Figure 6:
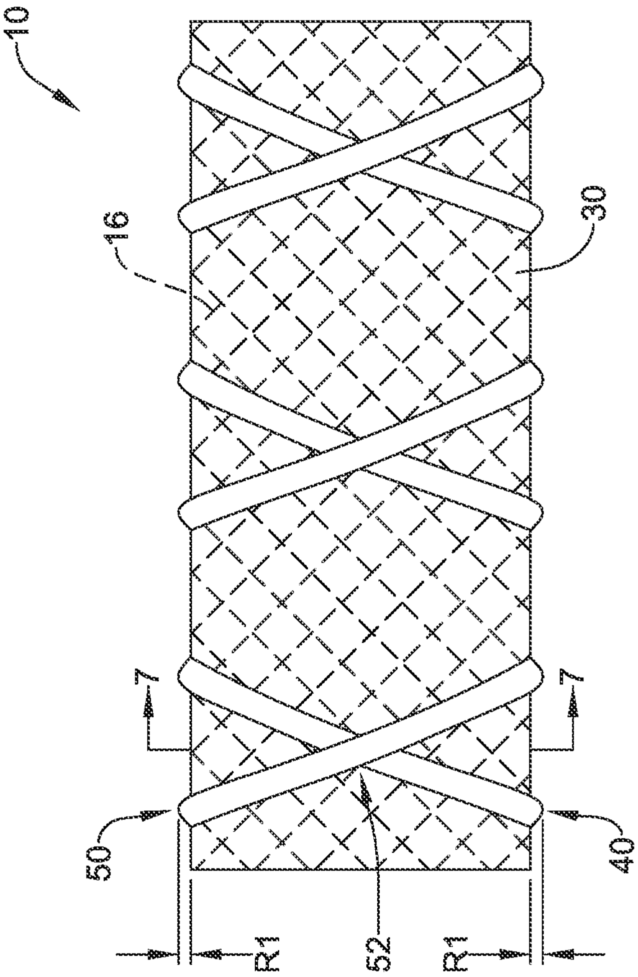
FIG. 6 illustrates selected aspects of an alternative configuration of the endoprosthesis of FIG. 1.

In some embodiments, the endoprosthesis 10 may include a second anti-migration element 50 extending radially outward from the tubular scaffold 16, as seen in FIG. 6. In some embodiments, the second anti-migration element 50 may extend radially outward from the outer surface (e.g., radially outward facing surface) of the polymeric covering 30. In some embodiments, the second anti-migration element 50 may be fixedly secured to, bonded to, or otherwise attached to the tubular scaffold 16 and/or the polymeric covering 30.

In at least some embodiments, the second anti-migration element 50 may extend helically along at least a portion of the length of the tubular scaffold 16 in a second helical direction (e.g., counterclockwise) opposite the first helical direction such that the anti-migration element 40 intersects with the second anti-migration element 50 at one or more, or a plurality of intersection points 52.

In some embodiments, the second anti-migration element 50 may be formed from a polymeric material. In some embodiments, the second anti-migration element 50 may be applied to and/or bonded to the outer surface of the polymeric covering 30 during a subsequent manufacturing step after the polymeric covering 30 has been applied to the tubular scaffold 16 and cured. In some embodiments, the second anti-migration element 50 may be formed from a polymeric bead of material applied over the polymeric covering 30. Some suitable but non-limiting materials for the second anti-migration element 50 and/or the polymeric bead of material, for example polymeric materials, are described below. In one non-limiting example, the second anti-migration element 50 and/or the polymeric bead of material may be formed from silicone or polyamide. In some embodiments, the second anti-migration element 50 and/or the polymeric bead of material may be formed from the same polymeric material as the polymeric covering 30 or a different polymeric material than the polymeric covering 30. In some embodiments, the second anti-migration element 50 may be formed from the same polymeric material as the anti-migration element 40 or a different polymeric material than the anti-migration element 40. Other configurations are also contemplated.

In some embodiments, the second anti-migration element 50 may be bioabsorbable and/or may include a bioabsorbable material. In some embodiments, the second anti-migration element 50 may include an adhesive material and/or a bioadhesive material, similar to the adhesive material and/or the bioadhesive material described herein with respect to the anti-migration element 40. In some embodiments, the second anti-migration element 50 may have a cross-sectional shape similar to the cross-sectional shape of the anti-migration element 40. In some embodiments, the second anti-migration element 50 may have a cross-sectional shape that is the same as the cross-sectional shape of the anti-migration element 40. In some embodiments, the second anti-migration element 50 may have a cross-sectional shape different from the cross-sectional shape of the anti-migration element 40. Structural characteristics and/or details related to the cross-sectional shape of the second anti-migration element 50 may be similar to those discussed herein with respect to the anti-migration element 40 and FIGS. 4A-4D and are not repeated in the interest of brevity.

In some embodiments, the anti-migration element 40 may extend a first radial distance R1 outward from the tubular scaffold 16 and/or the outer surface of the polymeric covering 30 between intersection points of the plurality of intersection points 52, as seen in FIG. 6. In some embodiments, the second anti-migration element 50 may extend the first radial distance R1 outward from the tubular scaffold 16 and/or the outer surface of the polymeric covering 30 between intersection points of the plurality of intersection points 52. In some embodiments, the anti-migration element 40 and the second anti-migration element 50 may each extend the first radial distance R1 outward from the tubular scaffold 16 and/or the outer surface of the polymeric covering 30 between intersection points of the plurality of intersection points 52.

Figure 7B:
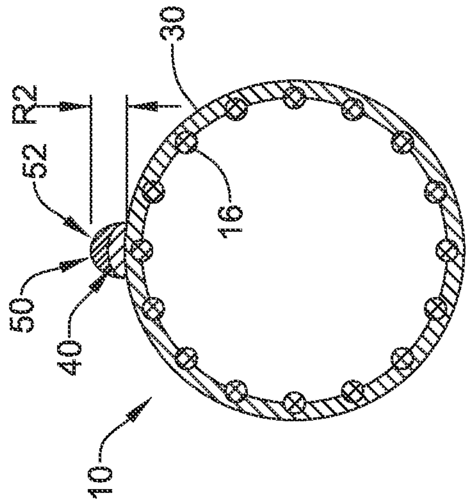
FIG. 7B is a partial cross-sectional view illustrating selected aspects of an alternative configuration of the endoprosthesis of FIG. 6.
Figure 7A:
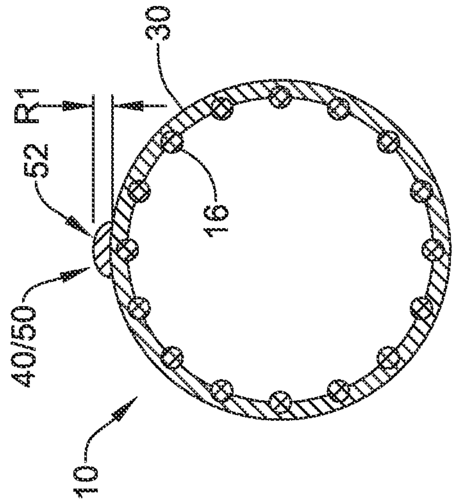
FIG. 7A is a partial cross-sectional view illustrating selected aspects of the endoprosthesis of FIG. 6.

In some embodiments, the plurality of intersection points 52 extend the first radial distance R1 outward from the tubular scaffold 16 and/or the outer surface of the polymeric covering 30, as seen in FIG. 7A. In some embodiments, at least some of the plurality of intersection points 52 extend the first radial distance R1 outward from the tubular scaffold 16 and/or the outer surface of the polymeric covering 30. In some embodiments, each of the plurality of intersection points 52 extends the first radial distance R1 outward from the tubular scaffold 16 and/or the outer surface of the polymeric covering 30. In at least some embodiments, the anti-migration element 40 and the second anti-migration element 50 intersect and do not overlap each other at the plurality of intersection points 52. As such, the first radial distance R1 is maintained at the plurality of intersection points 52.

In some embodiments, the plurality of intersection points 52 extend a second radial distance R2 outward from the tubular scaffold 16 and/or the outer surface of the polymeric covering 30, as seen in FIG. 7B. In some embodiments, at least some of the plurality of intersection points 52 extend the second radial distance R2 outward from the tubular scaffold 16 and/or the outer surface of the polymeric covering 30. In some embodiments, each of the plurality of intersection points 52 extends the second radial distance R2 outward from the tubular scaffold 16 and/or the outer surface of the polymeric covering 30. In at least some embodiments, the anti-migration element 40 and the second anti-migration element 50 intersect and overlap each other at the plurality of intersection points 52. For example, the second anti-migration element 50 may overlap the anti-migration element 40, or vice versa. As such, the plurality of intersection points 52 extends the second radial distance R2 outward from the tubular scaffold 16 and/or the outer surface of the polymeric covering 30. In some embodiments, the second radial distance R2 may be about twice the first radial distance R1. In some embodiments, the second radial distance R2 may be less than twice the first radial distance R1. Other configurations are also contemplated. In all embodiments where the second anti-migration element 50 overlaps the anti-migration element 40, or vice versa, the second radial distance R2 is greater than the first radial distance R1.

In some embodiments, the first radial distance R1 and/or the second radial distance R2 may be about 4.0 millimeters. In some embodiments where the second radial distance R2 is about 4.0 millimeters, the first radial distance R1 is less than 4.0 millimeters. In some embodiments, the first radial distance R1 and/or the second radial distance R2 may be about 3.5 millimeters. In some embodiments where the second radial distance R2 is about 3.5 millimeters, the first radial distance R1 is less than 3.5 millimeters. In some embodiments, the first radial distance R1 and/or the second radial distance R2 may be about 3.0 millimeters. In some embodiments where the second radial distance R2 is about 3.0 millimeters, the first radial distance R1 is less than 3.0 millimeters. In some embodiments, the first radial distance R1 and/or the second radial distance R2 may be about 2.5 millimeters. In some embodiments where the second radial distance R2 is about 2.5 millimeters, the first radial distance R1 is less than 2.5 millimeters. In some embodiments, the first radial distance R1 and/or the second radial distance R2 may be about 2.0 millimeters. In embodiments where the second radial distance R2 is about 2.0 millimeters, the first radial distance R1 is less than 2.0 millimeters. In some embodiments, the first radial distance R1 and/or the second radial distance R2 may be about 1.5 millimeters. In embodiments where the second radial distance R2 is about 1.5 millimeters, the first radial distance R1 is less than 1.5 millimeters. In some embodiments, the first radial distance R1 and/or the second radial distance R2 may be about 1.0 millimeters. In embodiments where the second radial distance R2 is about 1.0 millimeters, the first radial distance R1 is less than 1.0 millimeters. Other configurations are also contemplated.

Figure 8:
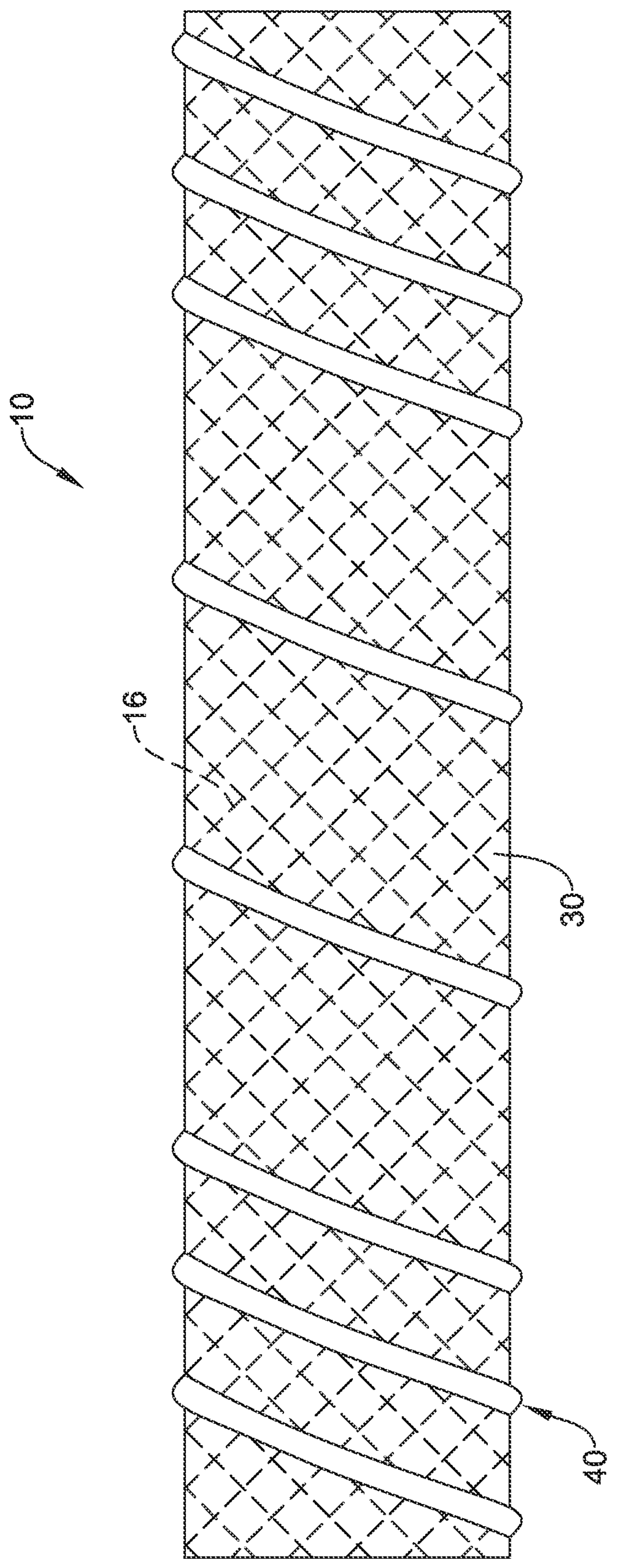
FIGS. 8-8A illustrate selected aspects of an alternative configuration of the endoprosthesis of FIG. 1.
Figure 8A:
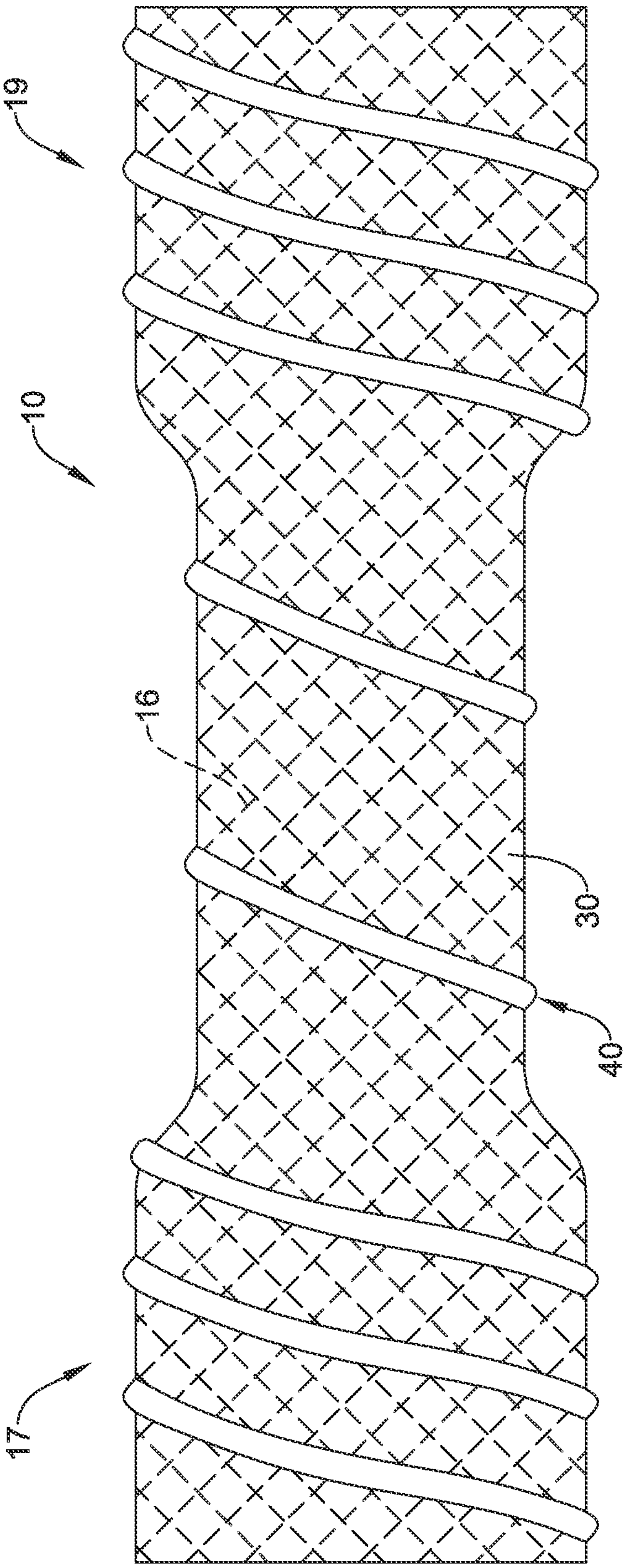

In some embodiments, a pitch between adjacent windings of the anti-migration element 40 and/or the second anti-migration element 50 may vary along the length of the tubular scaffold 16. In some embodiments, the pitch between adjacent windings of the anti-migration element 40 and/or the second anti-migration element 50 is wider and/or greater along the medial region and/or the body portion of the tubular scaffold 16 than the pitch between adjacent windings of the anti-migration element 40 and/or the second anti-migration element 50 along the proximal end region of the tubular scaffold 16 and/or the distal end region of the tubular scaffold 16, as seen in FIG. 8. In some embodiments, the pitch between adjacent windings of the anti-migration element 40 and/or the second anti-migration element 50 is wider and/or greater along the medial region and/or the body portion of the tubular scaffold 16 than the pitch between adjacent windings of the anti-migration element 40 and/or the second anti-migration element 50 along the flared first end portion 17 of the tubular scaffold 16 and/or the flared second end portion 19 of the tubular scaffold 16, as seen in FIG. 8A. In other embodiments, the pitch between adjacent windings of the anti-migration element 40 and/or the second anti-migration element 50 is wider and/or greater along the proximal end region of the tubular scaffold 16 and/or the distal end region of the tubular scaffold 16 than the pitch between adjacent windings of the anti-migration element 40 and/or the second anti-migration element 50 along the medial region and/or the body portion of the tubular scaffold 16. In some embodiments, the pitch between adjacent windings of the anti-migration element 40 and/or the second anti-migration element 50 is wider and/or greater along the flared first end portion 17 of the tubular scaffold 16 and/or the flared second end portion 19 of the tubular scaffold 16 than the pitch between adjacent windings of the anti-migration element 40 and/or the second anti-migration element 50 along the medial region and/or the body portion of the tubular scaffold 16. It is noted that the pitch of the other helical anti-migration elements described herein may also be varied along the length of the tubular scaffold 16 in a similar manor. Other configurations are also contemplated.

Figure 9:
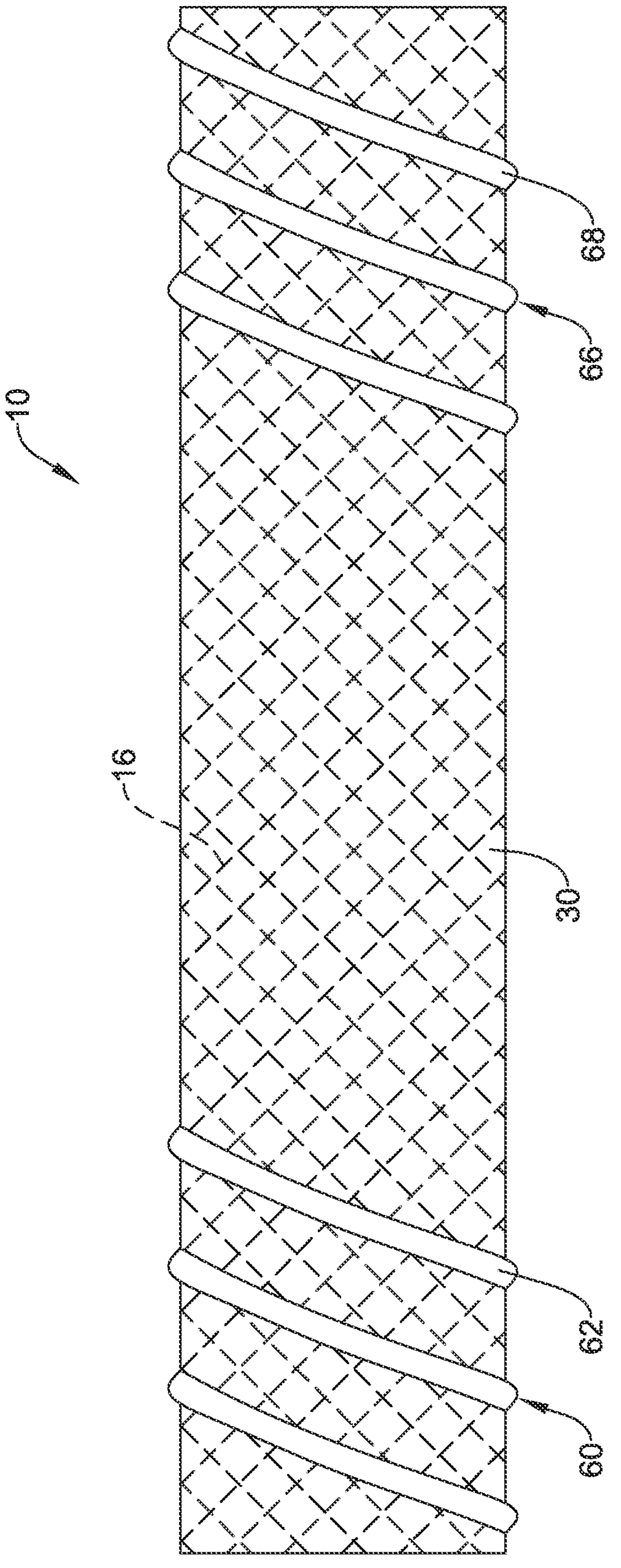
FIGS. 9-9A illustrate selected aspects of an alternative configuration of the endoprosthesis of FIG. 1.
Figure 9A:
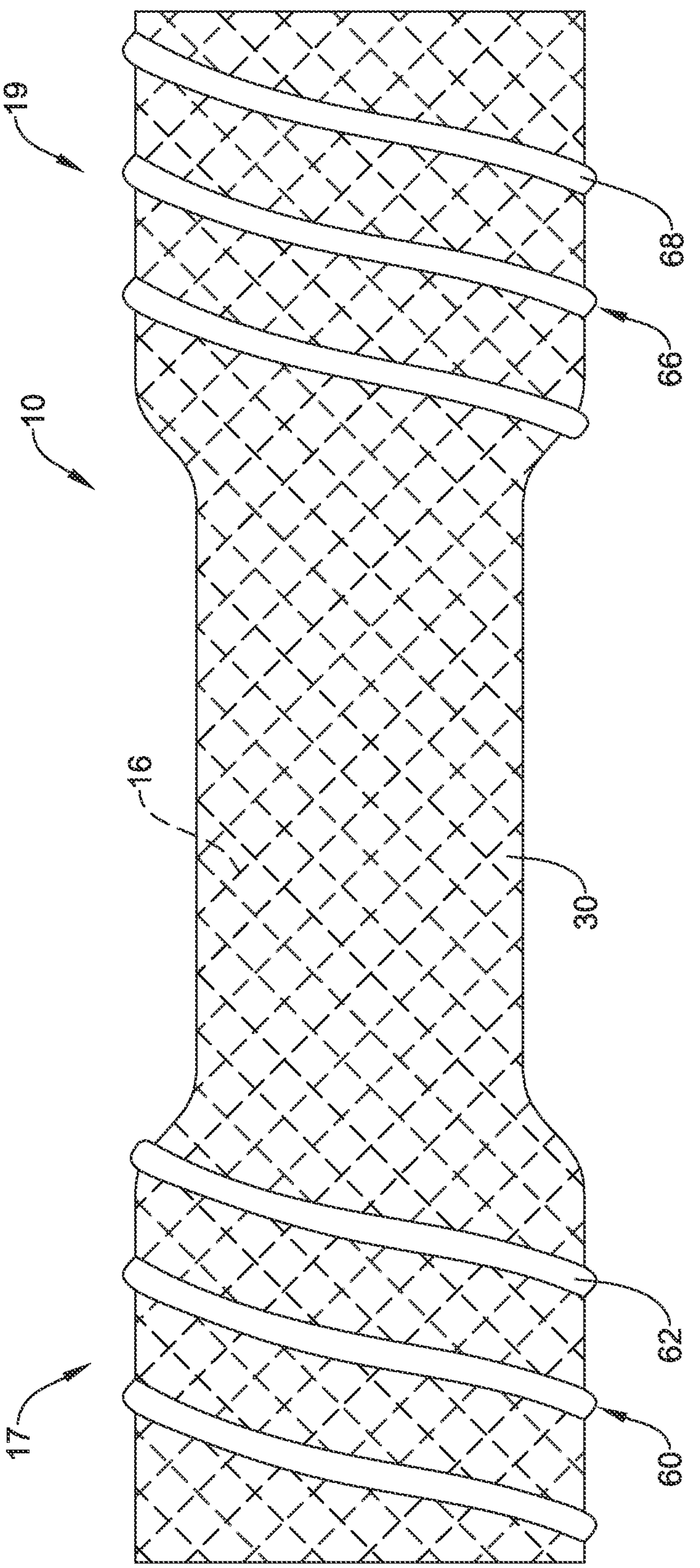

In some embodiments, the anti-migration element may include a proximal anti-migration element 60 including a first plurality of helical windings 62 disposed along the proximal end region of the tubular scaffold 16 and a distal anti-migration element 66 including a second plurality of helical windings 68 disposed along the distal end region of the tubular scaffold 16, the distal anti-migration element 66 being longitudinally spaced apart from the proximal anti-migration element 60 by the medial region of the tubular scaffold 16, as seen in FIG. 9. In some embodiments, the anti-migration element may include a proximal anti-migration element 60 including a first plurality of helical windings 62 disposed along the flared first end portion 17 of the tubular scaffold 16 and a distal anti-migration element 66 including a second plurality of helical windings 68 disposed along the flared second end portion 19 of the tubular scaffold 16, the distal anti-migration element 66 being longitudinally spaced apart from the proximal anti-migration element 60 by the medial region of the tubular scaffold 16, as seen in FIG. 9A. Other configurations are also contemplated.

A method of manufacturing the endoprosthesis 10 for implantation within a vessel lumen may include forming the tubular scaffold 16 from one or more interwoven filaments defining interstices therebetween, as described herein. The method may include applying the polymeric covering 30 to at least a portion of the tubular scaffold 16. In some embodiments, the method may include applying the polymeric covering 30 along the entire length of the tubular scaffold 16, such as via a spray coating or dip coating process.

Figure 10:
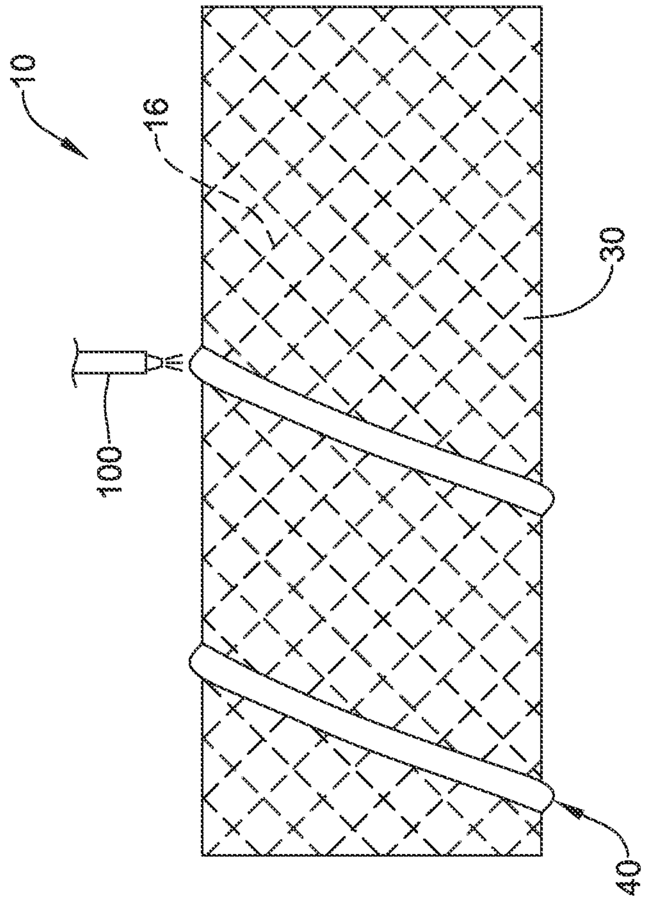
FIG. 10 illustrates selected aspects of a method of manufacturing the endoprosthesis of FIG. 1.

In some embodiments, the method of forming the endoprosthesis 10 may include positioning the tubular scaffold 16, previously coated with the polymeric covering 30, under a nozzle 100 configured to apply a polymeric bead of material onto the tubular scaffold 16 and/or the polymeric covering 30, as seen in FIG. 10. In some embodiments, the method may include applying the polymeric bead of material onto the tubular scaffold 16 and/or the polymeric covering 30 previously applied to the tubular scaffold 16 using the nozzle 100 such that the polymeric bead of material forms the anti-migration element 40 extending radially outward from the tubular scaffold 16 and/or the polymeric covering 30. In some embodiments, the method may include applying a second polymeric bead of material onto the tubular scaffold 16 and/or the polymeric covering 30 previously applied to the tubular scaffold 16 using the nozzle 100 such that the second polymeric bead of material forms the second anti-migration element 50 extending radially outward from the tubular scaffold 16 and/or the polymeric covering 30. In some embodiments, the method may include rotating and moving the tubular scaffold 16 longitudinally relative to the nozzle 100 as the polymeric material is expelled from the nozzle 100 to form the helical configuration of the anti-migration element 40 and/or the second anti-migration element 50. In some instance, the rotational and/or longitudinal speed may be held constant to provide a uniform pitch between windings of the anti-migration element and/or the second anti-migration element 50. In other instances, the rotational and/or longitudinal speed may be varied to vary the pitch between adjacent windings of the anti-migration element 40 (e.g., as seen in FIGS. 8-9A) and/or the second anti-migration element 50.

In some embodiments, the anti-migration element 40 may comprise a wire 70 extending along the outer surface 14 of the tubular scaffold 16 and/or an outer surface of the polymeric covering 30, as seen in FIGS. 11-16. In some embodiments, the wire 70 may be formed from a metallic material. In some embodiments, the wire 70 may be formed from a polymeric material. In some embodiments, the wire 70 may be formed from a composite material. In some embodiments, the tubular scaffold 16 and the wire 70 may both be formed from a metallic material. In some embodiments, the tubular scaffold 16 and the wire 70 may both be formed from a polymeric material. In some embodiments, the tubular scaffold 16 and the wire 70 may both be formed from a composite material. Other configurations, including but not limited to the tubular scaffold 16 and the wire 70 being formed from different materials, are also contemplated.

Figure 11:
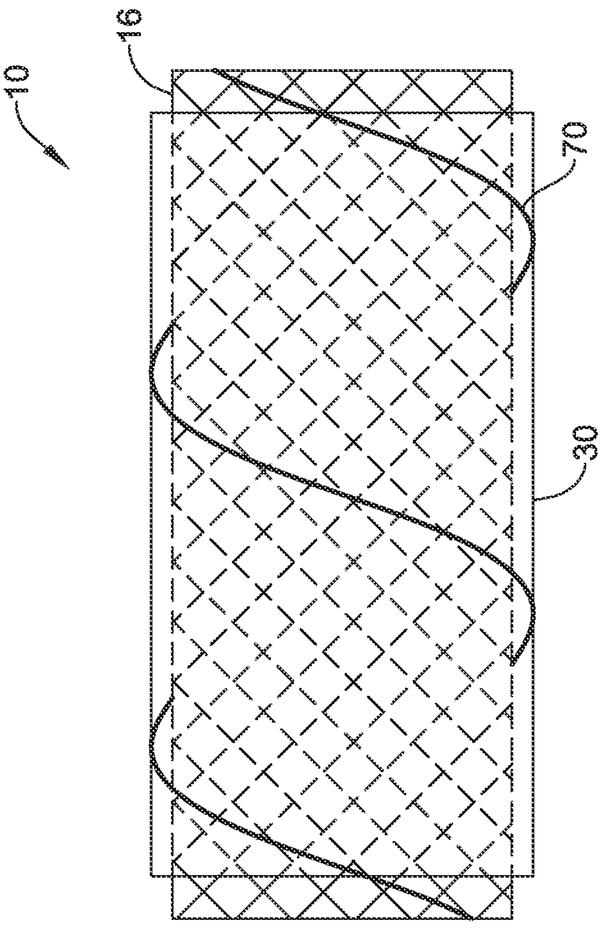
FIG. 11 illustrates selected aspects of an alternative configuration of the endoprosthesis of FIG. 1.

In some embodiments, a method of manufacturing the endoprosthesis 10 for implantation within a vessel lumen may include forming the tubular scaffold 16 from one or more interwoven filaments defining interstices therebetween, as described herein. The method may include applying the polymeric covering 30 to at least the medial portion of the tubular scaffold 16, as seen in FIG. 11, thus leaving the proximal and/or distal end regions of the tubular scaffold 16 bare or uncovered. In some embodiments, the method may include applying the polymeric covering 30 along the entire length of the tubular scaffold 16. In some embodiments, the method may include leaving at least a portion of the proximal end region and at least a portion of the distal end region of the tubular scaffold 16 uncovered by the polymeric covering 30 such that the proximal and/or end regions of the tubular scaffold 16 are bare. In some embodiments, the method may include wrapping the wire 70 helically around the tubular scaffold 16 over the polymeric covering 30, subsequent to applying the polymeric covering 30 to the tubular scaffold 16. In some embodiments, the method may include securing the wire 70 to uncovered portions of the tubular scaffold 16. In some embodiments, the uncovered portions of the tubular scaffold 16 may include the proximal end region disposed proximal of the medial region and/or the distal end region disposed distal of the medial region. In some embodiments, the method may include securing the wire 70 to uncovered portions of the proximal end region and the distal end region of the tubular scaffold 16. In some embodiments, securing the wire 70 to uncovered portions of the tubular scaffold 16 may include fixedly attaching, adhesive bonding, welding, brazing, reflowing, etc. the wire 70 to uncovered portions of the tubular scaffold 16.

Figure 12:
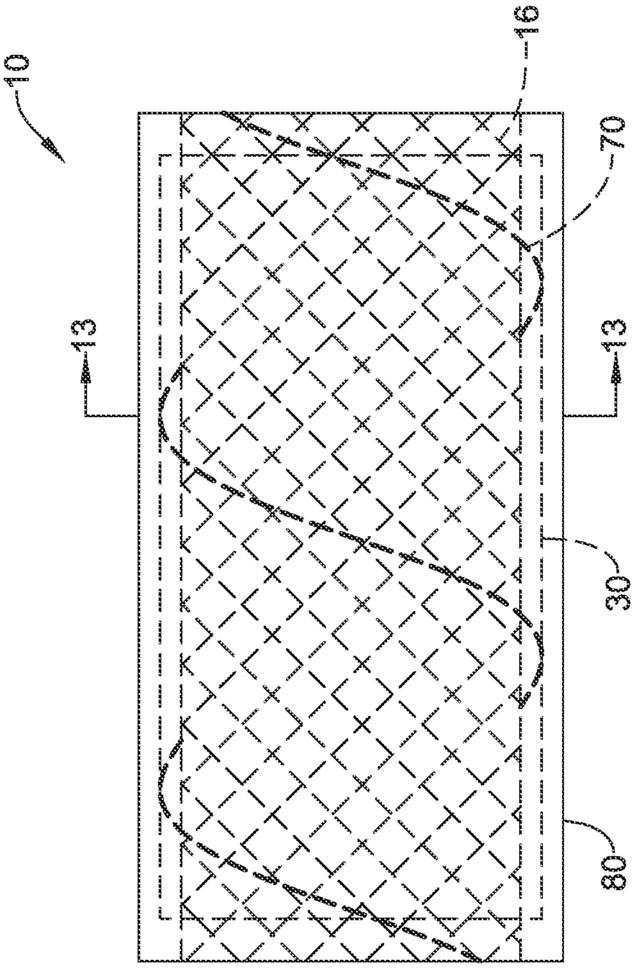
FIG. 12 illustrates selected aspects of the endoprosthesis of FIG. 11.
Figure 13:
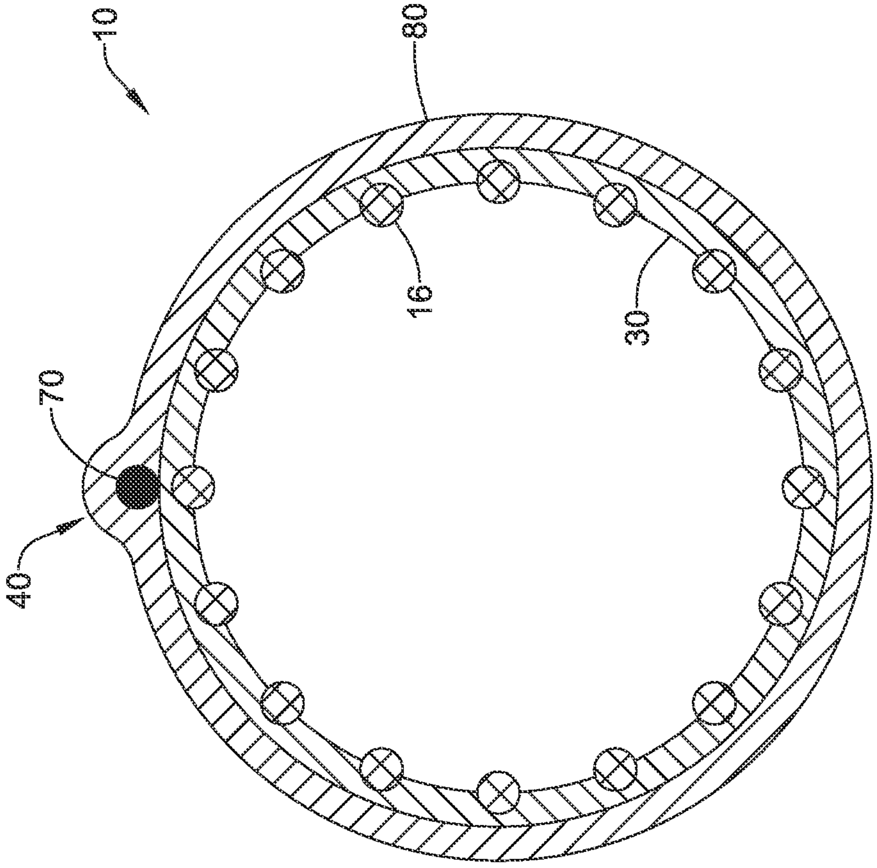
FIG. 13 is a partial cross-sectional view illustrating selected aspects of the endoprosthesis of FIGS. 11-12.

In at least some embodiments, the method may include thereafter applying a second polymeric covering 80 over the wire 70 and the polymeric covering 30, as well as the uncovered portions of the tubular scaffold 16, as seen in FIG. 12. In some embodiments, the method may include thereafter applying a second polymeric covering 80 over the wire 70 and the polymeric covering 30, as well as the uncovered portions of the proximal end region and the distal end region of the tubular scaffold 16. In some embodiments, applying the second polymeric covering 80 over the wire 70 may form and/or define the anti-migration element 40, as shown in FIG. 13. In some embodiments, the wire 70 may be at least partially embedded within and/or at least partially surrounded by the anti-migration element 40. In some embodiments, the tubular scaffold 16 and the wire 70 may be completely surrounded by and/or embedded within and/or between a combination of the polymeric covering 30 and the second polymeric covering 80.

Some suitable but non-limiting materials for the second polymeric covering 80, for example polymeric materials, are discussed below. In some embodiments, the second polymeric covering 80 may be formed as an additional layer of the polymeric covering 30. In some embodiments, the second polymeric covering 80 may be formed from the same polymeric material as the polymeric covering 30. In some embodiments, the second polymeric covering 80 may be formed from a different polymeric material than the polymeric covering 30. Other configurations are also contemplated.

Figure 14:
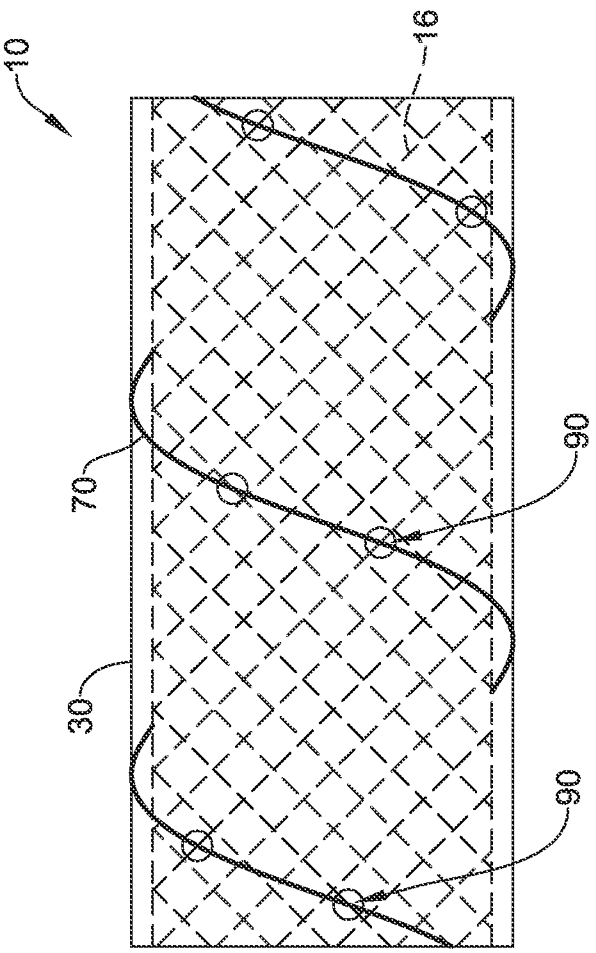
FIG. 14 illustrates selected aspects of an alternative configuration of the endoprosthesis of FIG. 1.

In some embodiments, a method of manufacturing the endoprosthesis 10 for implantation within a vessel lumen may include forming the tubular scaffold 16 from one or more interwoven filaments defining interstices therebetween, as described herein. The method may include applying the polymeric covering 30 to at least the medial portion of the tubular scaffold 16, as seen in FIG. 14, thus leaving the proximal and/or distal end regions of the tubular scaffold 16 bare or uncovered. In some embodiments, the method may include applying the polymeric covering 30 along the entire length of the tubular scaffold 16. In some embodiments, the method may include wrapping the wire 70 helically around the tubular scaffold 16 over the polymeric covering 30, subsequent to applying the polymeric covering 30 to the tubular scaffold 16. In some embodiments, the method may include securing the wire 70 to uncovered portions of the tubular scaffold 16. In some embodiments, the uncovered portions of the tubular scaffold 16 may include a plurality of attachment points 90 of the tubular scaffold 16 defined by removing some of the polymeric covering 30 from the tubular scaffold 16. In some embodiments, the plurality of attachment points 90 may include uncovered portions of the proximal end region disposed proximal of the medial region and/or the distal end region disposed distal of the medial region. In some embodiments, securing the wire 70 to uncovered portions of the tubular scaffold 16 may include securing the wire 70 to the tubular scaffold 16 at the plurality of attachment points 90. In some embodiments, securing the wire 70 to uncovered portions of the tubular scaffold 16 may include fixedly attaching, adhesive bonding, welding, brazing, reflowing, etc. the wire 70 to uncovered portions of the tubular scaffold 16. In some embodiments, securing the wire 70 to uncovered portions of the tubular scaffold 16 may include fixedly attaching, adhesive bonding, welding, brazing, reflowing, etc. the wire 70 to the tubular scaffold 16 at the plurality of attachment points 90.

Figure 15:
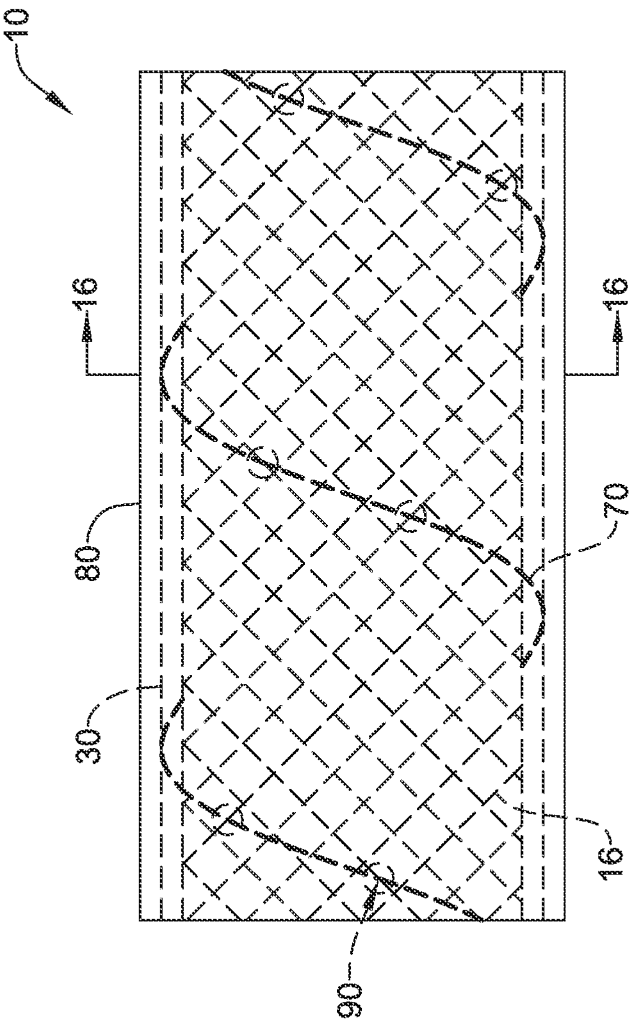
FIG. 15 illustrates selected aspects of the endoprosthesis of FIG. 14.
Figure 16:
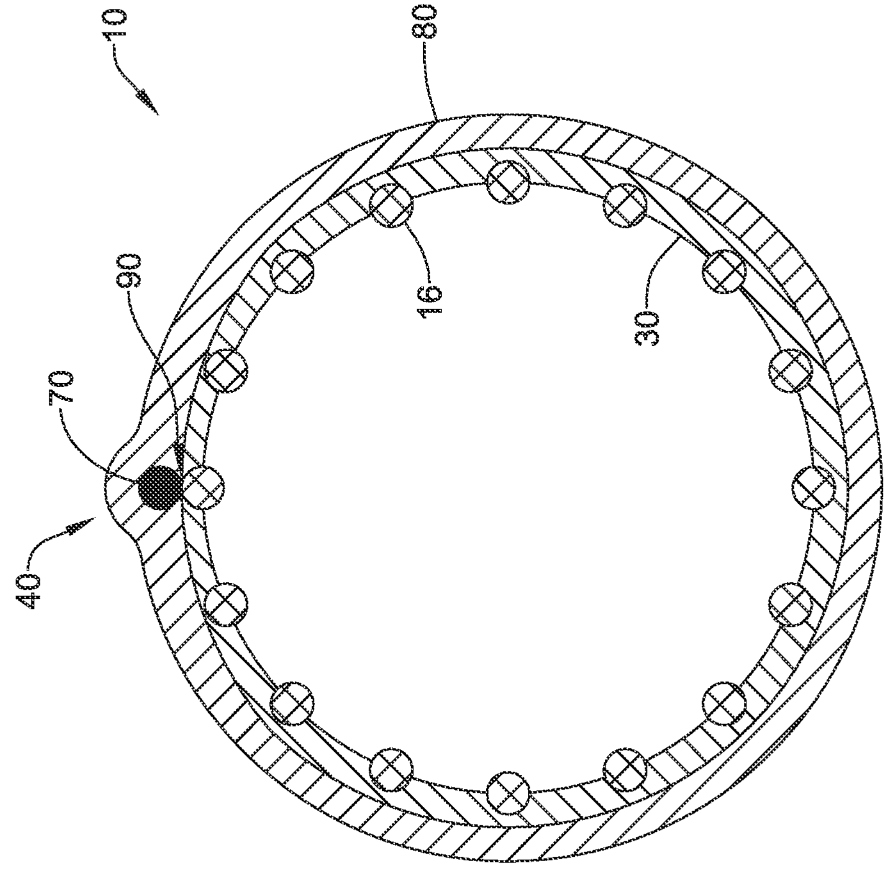
FIG. 16 is a partial cross-sectional view illustrating selected aspects of the endoprosthesis of FIGS. 14-15.

In at least some embodiments, the method may include thereafter applying a second polymeric covering 80 over the wire 70 and the polymeric covering 30, as well as the uncovered portions of the tubular scaffold 16, as seen in FIG. 15. In some embodiments, the method may include thereafter applying a second polymeric covering 80 over the wire 70 and the polymeric covering 30, as well as the plurality of attachment points 90. In some embodiments, applying the second polymeric covering 80 over the wire 70 and the plurality of attachment points 90 may form and/or define the anti-migration element 40, as shown in FIG. 16. In some embodiments, the wire 70 may be at least partially embedded within and/or at least partially surrounded by the anti-migration element 40. In some embodiments, the tubular scaffold 16 and the wire 70 may be completely surrounded by and/or embedded within and/or between a combination of the polymeric covering 30 and the second polymeric covering 80.

Some suitable but non-limiting materials for the second polymeric covering 80, for example polymeric materials, are discussed below. In some embodiments, the second polymeric covering 80 may be formed as an additional layer of the polymeric covering 30. In some embodiments, the second polymeric covering 80 may be formed from the same polymeric material as the polymeric covering 30. In some embodiments, the second polymeric covering 80 may be formed from a different polymeric material than the polymeric covering 30. Other configurations are also contemplated.

The materials that can be used for the various components of the system and the various elements thereof disclosed herein may include those commonly associated with medical devices. For simplicity purposes, the following discussion refers to the system. However, this is not intended to limit the system, devices, and/or methods described herein, as the discussion may be applied to other elements, members, components, or devices disclosed herein, such as, but not limited to, the endoprosthesis, the tubular scaffold, the polymeric covering(s), the anti-migration element(s), the wire, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN®), polyether block ester, polyurethane (for example, Polyurethane 85A), polypropylene (PP), polyvinylchloride (PVC), polyether-ester (for example, ARNITEL®), ether or ester based copolymers (for example, butylene/poly(alkylene ether) phthalate and/or other polyester elastomers such as HYTREL®), polyamide (for example, DURETHAN® or CRISTAMID®), elastomeric p polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID®), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, Elast-Eon® or ChronoSil®), biocompatible polymers, other suitable materials, or mixtures, combinations, copolymers thereof, polymer/metal composites, and the like. In some embodiments, the system and/or components thereof can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system and/or components thereof may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system and/or other elements disclosed herein. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum, or a Ni—Co—Cr-based alloy. The yarns may further include carbon, glass, or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An endoprosthesis for implantation within a vessel lumen, comprising:

a tubular scaffold having a length, the tubular scaffold formed of one or more interwoven filaments defining interstices therebetween, wherein the tubular scaffold is configured to shift between a radially collapsed configuration and a radially expanded configuration;

a polymeric covering secured to the tubular scaffold; and an anti-migration element extending radially outward from the tubular scaffold, wherein the anti-migration element comprises a wire extending along an outer surface of the polymeric covering;

wherein the anti-migration element extends helically along at least a portion of the length of the tubular scaffold in a first helical direction;

wherein a second polymeric covering is disposed over the wire and forms at least a portion of the anti-migration element.

2. The endoprosthesis of claim 1, wherein the wire is secured directly to the tubular scaffold at a plurality of attachment points.

3. The endoprosthesis of claim 2, wherein the second polymeric covering is disposed over the plurality of attachment points.

4. The endoprosthesis of claim 1, wherein the anti-migration element extends continuously from a proximal end of the anti-migration element to a distal end of the anti-migration element.

5. The endoprosthesis of claim 1, wherein a pitch between adjacent windings of the anti-migration element varies along the length of the tubular scaffold.

6. The endoprosthesis of claim 5, wherein the pitch between adjacent windings of the anti-migration element is wider along a medial region of the tubular scaffold than the pitch between adjacent windings of the anti-migration element along a proximal end region of the tubular scaffold and/or a distal end region of the tubular scaffold.

7. The endoprosthesis of claim 2, wherein the plurality of attachments points is disposed at uncovered portions of the tubular scaffold.

8. The endoprosthesis of claim 7, wherein the uncovered portions of the tubular scaffold include at least a portion of a proximal end region of the tubular scaffold and at least a portion of a distal end region of the tubular scaffold.

9. The endoprosthesis of claim 7, wherein at least some of the uncovered portions of the tubular scaffold are disposed along a medial region of the tubular scaffold.

10. The endoprosthesis of claim 2, wherein the tubular scaffold and the wire are both formed from a metallic material.

11. The endoprosthesis of claim 10, wherein the wire is fixedly attached to the tubular scaffold at the plurality of attachment points.

12. The endoprosthesis of claim 11, wherein the wire is welded to the tubular scaffold at the plurality of attachment points.

13. The endoprosthesis of claim 1, wherein the one or more interwoven filaments extend radially inward of an inner surface of the first polymeric covering.

14. The endoprosthesis of claim 1, wherein the second polymeric covering extends around an entire circumference of the tubular scaffold within a cross-sectional plane taken perpendicular to a central longitudinal axis of the tubular scaffold.

15. The endoprosthesis of claim 1, wherein an outer surface of the wire is disposed in contact with the outer surface of the polymeric covering.

16. A method of manufacturing an endoprosthesis for implantation within a vessel lumen, comprising:

forming a tubular scaffold from one or more interwoven filaments defining interstices therebetween, the tubular scaffold having a length;

applying a polymeric covering to at least a portion of the tubular scaffold;

positioning the tubular scaffold under a nozzle configured to apply a polymeric bead of material onto the polymeric covering; and applying the polymeric bead of material onto the polymeric covering previously applied to the tubular scaffold using the nozzle such that the polymeric bead of material forms an anti-migration element extending radially outward from the polymeric covering, wherein the anti-migration element extends helically along at least a portion of the length of the tubular scaffold.

17. The method of claim 16, further comprising:

rotating and moving the tubular scaffold longitudinally relative to the nozzle to vary a pitch between adjacent windings of the anti-migration element.

18. A method of manufacturing an endoprosthesis for implantation within a vessel lumen, comprising:

forming a tubular scaffold from one or more interwoven filaments defining interstices therebetween, the tubular scaffold having a length;

applying a polymeric covering to at least a medial region of the tubular scaffold;

wrapping a wire helically around the tubular scaffold over the polymeric covering;

securing the wire to uncovered portions of the tubular scaffold; and thereafter, applying a second polymeric covering over the wire and the uncovered portions of the tubular scaffold.

19. The method of claim 18, wherein the uncovered portions of the tubular scaffold include a proximal end region disposed proximal of the medial region and a distal end region disposed distal of the medial region.

20. The method of claim 18, wherein the uncovered portions of the tubular scaffold include a plurality of attachment points of the tubular scaffold defined by removing some of the polymeric covering from the tubular scaffold;

wherein securing the wire to uncovered portions of the tubular scaffold includes securing the wire to the tubular scaffold at the plurality of attachment points.

* * * * *